(12) United States Patent
Wootton

(10) Patent No.: US 9,568,436 B2
(45) Date of Patent: Feb. 14, 2017

(54) SYSTEM AND METHOD FOR DECORATION INSPECTION ON TRANSPARENT MEDIA

(71) Applicant: ATS AUTOMATION TOOLING SYSTEMS INC., Cambridge (CA)

(72) Inventor: Gerald Wootton, Cambridge (CA)

(73) Assignee: ATS AUTOMATION TOOLING SYSTEMS INC., Cambridge, Ontario (CA)

( * ) Notice: Subject to any disclaimer, the term of this patent is extended or adjusted under 35 U.S.C. 154(b) by 0 days.

(21) Appl. No.: 14/489,544

(22) Filed: Sep. 18, 2014

(65) Prior Publication Data

US 2015/0077742 A1    Mar. 19, 2015

Related U.S. Application Data

(60) Provisional application No. 61/879,406, filed on Sep. 18, 2013.

(51) Int. Cl.
```
G01N 21/00    (2006.01)
G01N 21/88    (2006.01)
G01N 21/958   (2006.01)
```

(52) U.S. Cl.
CPC ........ *G01N 21/8806* (2013.01); *G01N 21/958* (2013.01); *G01N 2021/8835* (2013.01); *G01N 2021/8848* (2013.01)

(58) Field of Classification Search
CPC .... G01N 21/00; G01N 13/00; G01N 2201/00; G01B 11/00; G03F 1/00; H01L 22/00; G06T 7/00
USPC ................................. 356/237.2–237.6, 239.3
See application file for complete search history.

(56) References Cited

U.S. PATENT DOCUMENTS

| | | | | |
|---|---|---|---|---|
| 6,021,105 A * | 2/2000 | Choi | ............... | G11B 7/0908 |
| | | | | 369/112.28 |
| 6,064,477 A * | 5/2000 | Matsumoto | ............ | G01N 21/94 |
| | | | | 356/237.2 |
| 7,728,965 B2 * | 6/2010 | Haller | ................ | G01N 21/8806 |
| | | | | 356/237.1 |
| 7,773,212 B1 * | 8/2010 | Wolters | .............. | G01N 21/9501 |
| | | | | 356/237.4 |
| 7,919,760 B2 * | 4/2011 | Jau | .......................... | H01J 37/20 |
| | | | | 250/310 |
| 8,210,742 B2 * | 7/2012 | Moriya | ............... | G01M 99/002 |
| | | | | 356/237.3 |
| 2004/0207836 A1 * | 10/2004 | Chhibber | ........... | G01N 21/4738 |
| | | | | 356/237.4 |

(Continued)

*Primary Examiner* — Tarifur Chowdhury
*Assistant Examiner* — Isiaka Akanbi
(74) *Attorney, Agent, or Firm* — Gowling WLG (Canada) LLP; Neil Henderson

(57) ABSTRACT

There is provided a system for inspecting an edge area of a transparent media, the transparent media having a decoration on a surface, the system includes: an illuminator to direct light to the transparent media for inspection, wherein the illuminator directs light to the transparent media at an oblique angle relative to a surface of the transparent media which is opposite the surface with the decoration; an optical element to capture light transmitted through the transparent media; and a sensor to obtain an image from the light captured by the optical element. There is also provided a method for inspecting an edge area of a transparent media, where the transparent media has a decoration on a surface.

17 Claims, 12 Drawing Sheets

(56) References Cited

U.S. PATENT DOCUMENTS

| | | | |
|---|---|---|---|
| 2008/0088830 A1* | 4/2008 | Serikawa | G01N 21/958 356/237.2 |
| 2009/0122304 A1* | 5/2009 | Jin | G01N 21/9503 356/237.4 |
| 2010/0053603 A1* | 3/2010 | Sakaguchi | G01B 11/30 356/237.4 |
| 2014/0253910 A1* | 9/2014 | Lewis | G01N 21/9515 356/237.5 |
| 2014/0261170 A1* | 9/2014 | Chen | B65H 23/0216 118/668 |

* cited by examiner

SYSTEM AND METHOD FOR DECORATION INSPECTION ON TRANSPARENT MEDIA

FIELD

The present disclosure relates generally to systems and methods for the inspection of decorations of transparent media. More particularly, the present disclosure relates to methods and systems for the inspection of decorations that are in close proximity to or overlying the edge of the transparent media.

BACKGROUND

Cover glass for watches, mobile communication devices, displays and computing devices is commonly decorated with one or more layers of ink, paint or other materials. Decoration is done for graphic effect and/or to reduce or modify the transparency of the cover glass. Although commonly referred to as "cover glass", the covering may be any one of a number of transparent media. Also, the decoration may be composed of layers of various materials that have been applied by a variety of means including screen print, direct print, stenciling, among others.

In some applications it is desirable to continue decoration onto the edges of the transparent media. This may include decorating edge features such as chamfers or other edge finishing details. In a manufacturing process, it is generally desirable to inspect decoration features for various attributes, for example, opacity, edge quality, and location. This inspection typically includes portions of decoration that extend onto the edges of the transparent media.

Currently, inspection of the edges of transparent media is commonly practiced for the detection and measurement of chips, cracks and other defects. Existing edge inspection systems are designed to emphasize and enhance the appearance of edge contours and common defects such as chips, scratches, and cracks. This type of inspection is typically accomplished prior to decoration. However, since parts with minor imperfections (chips, scratches, cracks and the like) may still be considered acceptable, inspection systems intended to inspect decoration should be able to work well with moderately damaged parts. For various reasons described in more detail below, inspection systems that are intended primarily for inspecting edge quality generally do not work well when used to inspect decoration of the edges. For example, these types of inspection systems typically make defects highly visible, which may obscure and make the decoration less visible for inspection. Additionally, this type of inspection system may make it difficult to discriminate defects in decoration from other types of defects.

In inspection, different conventional imaging methods may be employed, such as: backlighting, which tends to make defects appear as dark features; dark field lighting (oblique light), which tends to make defects appear as bright features; front lighting; and structured lighting, which reveals the edge profile.

Conventional backlighting can be problematic because edge contours and surface defects may direct light away from the image sensor resulting in dark areas in the image. As such, a dark line will generally appear along the edge of the glass, which interferes with the measurement of the coverage of decoration at the edge of the glass. As well, since illumination passes through the edge contours on both sides, the edge contour opposite the one being inspected may have an undue effect on the resulting image.

Conventional dark field lighting can be problematic because the margins of the decoration along an edge contour may be essentially invisible due to the decorations being far from normal to the direction of image acquisition. Also, dark field lighting emphasizes minor defects such as surface texture, scratches, cracks, and dust, which detracts from locating decoration edge contours. Additionally, dark field lighting cannot generally provide a measure of opacity.

Conventional front lighting is generally not suitable for decoration inspection because it is affected by gloss and highlights, particularly if the decoration is wet. In-line inspection is similarly not suitable because the decoration is typically freshly applied and still wet and glossy, while various artifacts, such as gas bubbles and screen print fabric texture, have not yet leveled out.

Conventional side lighting, wherein the transparent media is illuminated from the side, is also generally not suitable because this type of lighting may result in uneven contrast due to variable gloss and can result in flares from edge chips. These detrimental outcomes are particularly noticeable on dark or black decoration. Additionally, front lighting and side lighting are generally not desirable as they are unable to provide a measure of opacity, which is typically used to determine the thickness of decoration.

In conventional systems, decoration is typically inspected with backlight since, in addition to revealing location and quality of patterned features, backlighting permits the opacity of the decoration to be judged. Additionally, multi-spectral illumination and/or optical sensing may be used to measure spectral transmittance. Front lighting may also be used in order to also measure decoration color and/or reflectance. Typically, this sort of inspection is not done at or near edges and particularly places where the decoration comes near or wraps around the edges as these inspection systems generally do not perform well in these locations.

Some edge inspection systems use structured light in order to inspect the edges of a glass. This type of system resolves the edge into a 3-D profile. However, this type of system may not be able to determine the quality of decoration in the edge area because the edge area is typically contoured (by, for example, a chamfer or radius) and decoration layers are typically only a few microns thick. Additionally, the edge area may have some surface imperfections due to machining which may produce edge defects, such as small chips, that are within acceptable ranges for cover glass quality control. As well, this type of inspection system cannot make a measurement of opacity. Furthermore, while the important aspect of decoration coverage is the deposition of the more opaque pigments, binders tend to migrate from the decoration which makes edge contours less distinct.

Typically, due to the aforementioned reasons, existing inspection systems used to assess transparent media quality, and in particular the quality of decoration, may not be sufficient to accurately qualify decoration over edge features and accurately measure decoration coverage. As such an improved inspection system and method are required.

SUMMARY

As such there is a need for a system and/or method that are intended to overcome at least one of the above described disadvantages.

In one aspect described herein, there is provided a system for inspecting an edge area of a transparent media, the transparent media having a decoration on a surface, the system includes: an illuminator to direct light to the transparent media for inspection, wherein the illuminator directs light to the transparent media at an oblique angle relative to a surface of the transparent media which is opposite the surface with the decoration; an optical element to capture light transmitted through the transparent media; and a sensor to obtain an image from the light captured by the optical element.

In one case, the edge area of the transparent media may have a shaped profile. For example, a profile that is not a typical right-angled edge. In particular, the shaped profile may be curved, chamfered, or radiused.

In another case, the illuminator may be configurable to vary the intensity of the directed light to uniformly illuminate the edge area of the transparent media.

In a further case, the system may further include a polarizer that modifies the polarity of the light from the illuminator.

In a further case, the system may further include a formatter that alters the distribution of the light which illuminates the transparent media.

In a further case, the system may further include at least one mirror that bends the optical path of the light from the illuminator to allow for adjustment of the transparent media.

In a further case, the system may further include a handler to hold the transparent media.

In a further case, the system may further include a fixture for supporting the transparent media, wherein the fixture allows light from the illuminator to at least partially pass through the fixture. In this case, the fixture may include an optical modifier element formed into the fixture to modify the light from the illuminator.

In yet another case, the edge area of the transparent media may be an interior edge of the transparent media.

In yet another case, the illuminator may be a generally circular shape.

In yet another case, the illuminator may further include auxiliary optics.

According to another aspect, there is provided a method for inspecting an edge area of a transparent media, the transparent media having a decoration on a surface, the method includes: positioning an illuminator for directing light at the transparent media, wherein the illuminator directs light at the transparent media at an oblique angle relative to a surface of the transparent media which is opposite the surface with the decoration; positioning an optical element to capture light transmitted through the transparent media; and obtaining an image of the transparent media with a sensor from the light captured by the optical element.

In one case, the method may further include configuring the intensity of the directed light from the illuminator to uniformly illuminate the edge area of the transparent media.

In another case, the illuminator may be positioned such that it is not within the field of view of the optical element except by bending of the directed light by the transparent media.

In another case, the method may further include placing a formatter between the illuminator and the transparent media to alter at least one of the distribution, angle, or polarization of the directed light.

In another case, the edge area of the transparent media may be an interior edge of the transparent media.

In another case, the optical element may be positioned to keep substantially all light emitted from the transparent media within the acceptance angle of the optical element.

In another case, the illuminator may be positioned such that the directed light impinges on the edge of the transparent media and is refracted through the edge area of the surface having decoration towards the optical element.

Further aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
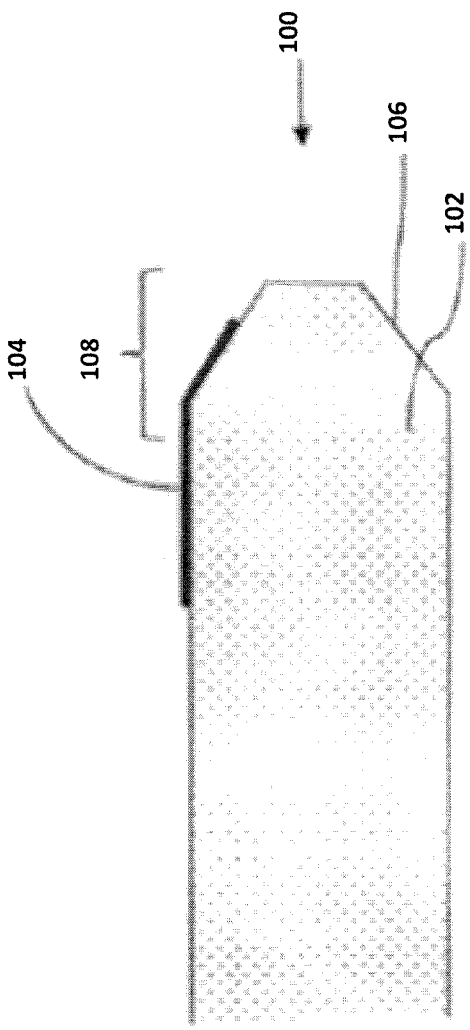
FIG. 1 is a cross-sectional view showing a detailed view of a section of an edge of a decorated transparent media.

Numerous specific details are set forth in order to provide a thorough understanding of the example embodiments described herein. However, it will be understood by those of ordinary skill in the art that the embodiments described herein may be practiced without all specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein. The embodiments described herein are not intended to be limited to the specific details of any one example embodiment or to specific details that may be common to multiple, or all, example embodiments. The applicants, inventors or owners reserve all rights that they may have in any embodiments disclosed herein, for example the right to embodiments claimed in a continuing application, and do not intend to abandon, disclaim or dedicate to the public any such embodiments by disclosure of this document.

While the disclosed embodiments generally relate to cover glass, use with any type of glass or other transparent or semi-transparent media is contemplated.

In an embodiment, the present disclosure is directed to a system and method for inspection on transparent media. Generally, the inspection is capable of measuring transparent media decoration edge coverage. The system includes an off-axis backlight, an image sensor with lens and an image processing system or observer. The light is arranged to provide useful illumination through the transparent media using the transparent media edge contour. The lens and image acquisition path are arranged to capture a substantial portion of the illumination not occluded by transparent media decoration. Additional lighting may be provided in order to further classify any decoration defect in relation to transparent media defect. In this system, the resulting image is intended to display the decoration as highly visible as possible while also suppressing unwanted artifacts, flaws or defects in the edge itself.

In another embodiment, the present disclosure is directed to a system and method for edge decoration inspection of transparent media. The system and method largely comprises inputting or transmitting light into the transparent media at an oblique angle from a side opposite the decorated surface. By refraction, the light impinges on the edge of the transparent media internally and is refracted through the edge contour on the decorated side towards an image sensor. The central angle of the illumination may be optimized in accordance with the angle of the edge chamfer such that the angle includes a sufficiently broad distribution to produce an image with a desired amount of the decoration. This large angle is used in order to cover a range of surface orientations, including those resulting from minor defects. The image sensor may have a generally large numerical aperture (a large range of angles over which the system can accept or emit light) in order to collect light over a relatively broad range of angles. Due to edge contours, most of the light being sensed is directed somewhat outward from the edge, and consequently, the light collecting lens is preferably placed with its principle axis outside the edge being inspected thereby using lens parallax to an advantage.

In the systems and methods described herein, the transparent media is generally presented for examination at a predetermined location relative to the inspection assembly. Inspection is performed either by visual inspection of the resulting image or by automated inspection using a machine vision system. The transparent media may be moved relative to the inspection optics or vice-versa such that a greater portion of the edges of the transparent media may be inspected. Certain inspections and/or determinations may be made, including: the quality of the edges of the decoration; the location of the edges of the decoration relative to the edge of the transparent media or other locations; the opacity of the decoration; and the like.

It will be understood that the systems and methods described herein may also be applied to interior edges associated with apertures in a transparent media. It will be further understood that the systems and methods may include: polarizers; optical devices that modify the distribution of the illumination; mirrors or prisms, which bend or compress the optical path; and the like. The illuminator, imaging device and other modules may be moveable or controllable in order to vary the overall inspection conditions, such as the spectrum, polarity, and angle of incidence.

FIG. 1 illustrates an exemplary cross-sectional view of a section of an edge of transparent media 100. In some embodiments, an edge 102 of the transparent media 100 may have a shaped profile. In this example, the shaped profile of the edge 102 includes a bottom-side chamfer 106 and a top-side chamfer 108. The top side of the transparent media 100 has decoration 104 applied to it. In many cases, the area that requires inspection is the top-side chamfer edge 108.

Figure 2:
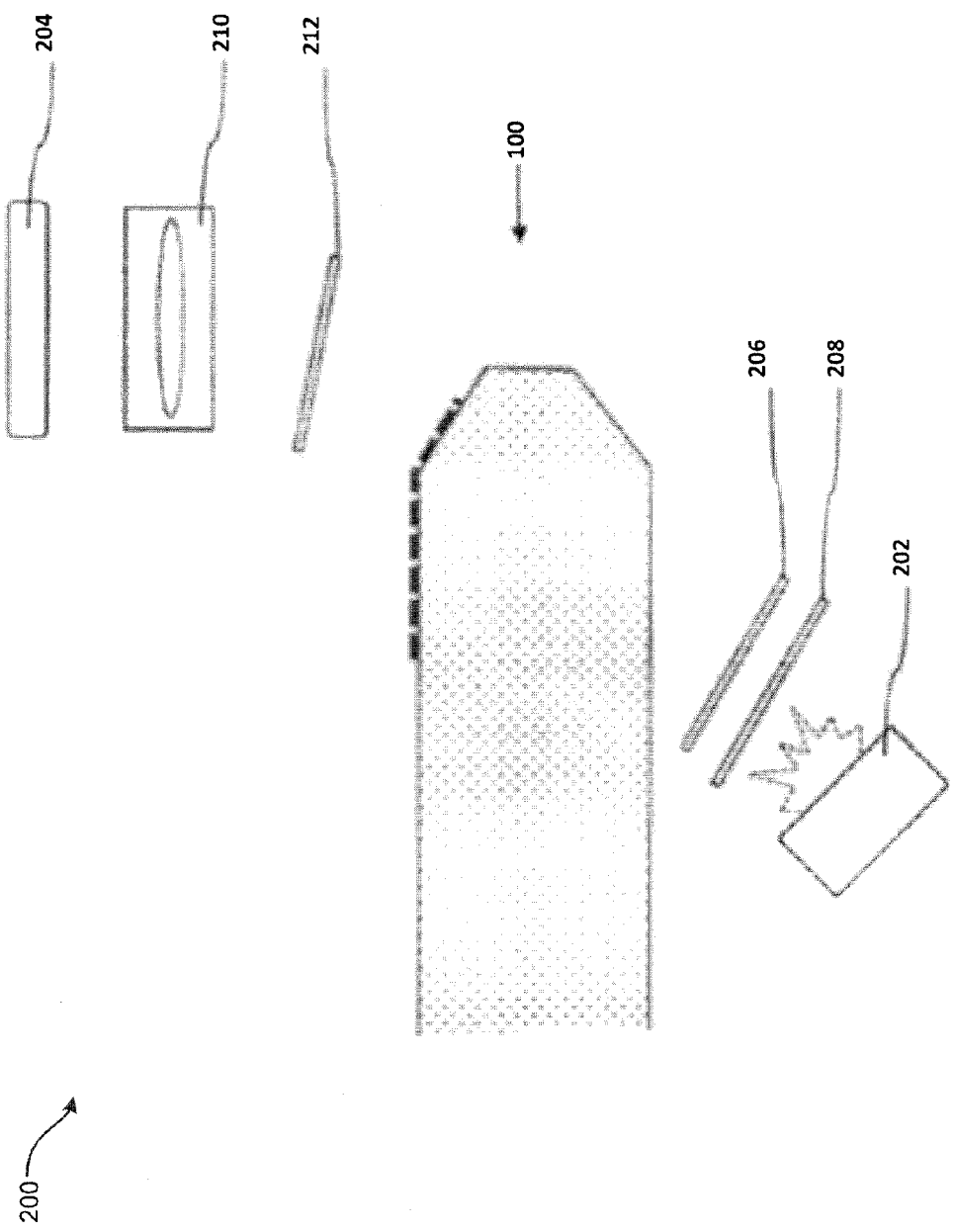
FIG. 2 is a cross-sectional view showing an embodiment of the general arrangement of illumination and sensing optics used for inspecting decoration near the edge of the transparent media.

FIG. 2 illustrates a cross-sectional view of a system 200 for transparent media edge decoration inspection, according to an embodiment. In this embodiment, an arrangement of illumination and sensing optics are used for inspecting decoration near the edge of the transparent media 100. The system 200 includes an illuminator 202, a sensor 204, a polarizer 206, a formatter 208, an objective 210 and an analyzer 212.

The transparent media 100 is placed above the illuminator 202. The illuminator 202 is a light source used to direct light towards the edge of the transparent media 100 for inspection purposes. The illuminator 202 may be single or multi-spectral. Located between the transparent media 100 and the illuminator 202 are the polarizer 206 and the formatter 208. The polarizer 206 may be used to either achieve a preferred polarization or to vary polarization during inspection. The polarizer 206 may be a variable-type polarizer. The edge contours of the transparent media 100 transmit light depending on the polarity of the light; particularly, it may depend on whether the edge contour is oblique to the path of the light. This property can be used to further examine the edge contour of the transparent media 100.

The formatter 208 is used to constrain the directed light coming from the illuminator 202. The formatter 208 may constrain the directed light to illuminate a certain shaped area, modify the angular distribution of the illumination, or the like. The distribution of practical light is thus improved by the insertion of masking or refractive elements at the formatter 208. The formatter 208 may be fixed or be comprised of interchangeable elements, for example, a series of apertures, lenses, or holograms.

Located above the transparent media 100 are the objective 210, the sensor 204 and the analyzer 212. The objective 210 is an optical element that is used to capture light transmitted through the transparent media 100 and transfer it to the sensor 204. In further cases, any suitable optical element may be used. The sensor 204 is used to obtain measurements. The sensor 204 could be a human assist device, such as a microscope eyepiece or video microscope, or an automated device, such as an image sensor coupled to a machine vision system. In some cases, the system 200 may include an analyzer 212. The analyzer 212 is a fixed or variable polarizing element that may be used alone or in conjunction with the polarizer 206. In some cases, the analyzer 212 may be used to measure optical properties such as intensities, polarization, spectrum, or the like.

Figure 3:
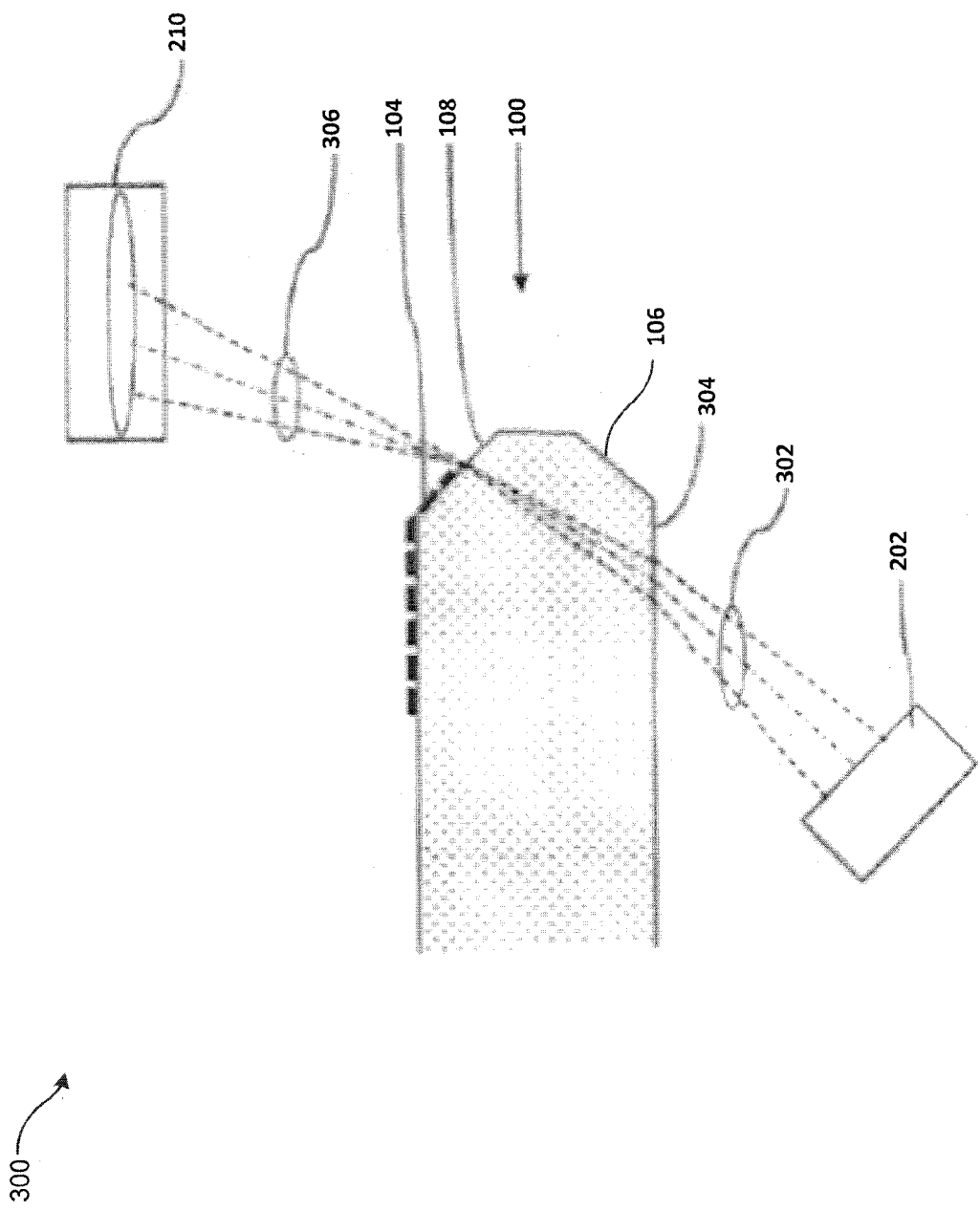
FIG. 3 is a cross-sectional view showing the general optic arrangement according to one embodiment.

FIG. 3 shows the general optical arrangement of an embodiment of a system for the inspection of transparent media edge decoration. In this embodiment, the system 300 includes the illuminator 202 and the objective 210. The illuminator 202 directs off-axis light that passes through the transparent media 100 away from the bottom edge contour 106. The directed light illuminates the second edge contour 108 and, being redirected by refraction, is emitted within the acceptance angle of the objective 210. This permits the directed light to be transferred to a sensor whereby an image of the surface of the second edge contour 108, including the decoration 104, is formed.

The illuminator 202 is a light source that is used to direct light towards the edges of the transparent media for inspection. The illuminator 202 provides directed light 302 with an angular distribution and positioned such that it is not within the field of view of the objective 210, except when the light is bent while passing through the transparent media 100. The illuminator 202 is positioned such that although it is in a backlighting configuration, it does not directly illuminate the field of the objective 210. In further cases, the illuminator 202 may incorporate various optical devices in order to achieve the desired light distribution; for example, the formatter 208 described with reference to FIG. 2.

The directed light 302 is directed towards the transparent media at an oblique angle, within a predetermined range of angles. In the example of FIG. 3, light directed towards a single point on the top-side edge contour 108 is shown. In further cases, the directed light 302 is only required to be emitted as a beam sufficiently wide to at least illuminate the entire edge portion of the transparent media 100. The range of angles effectively determines the numerical aperture of the sensing elements and consequently the depth of focus of the objective 132 in the case that it is used to produce an image of the top-side edge contour 108. A limited angular distribution is shown for each point; however, the illuminator 202 or the effective aperture of the objective 132, or both, may be used to determine the effective cone of light used to illuminate edge points of the transparent media 100.

The directed light 302 is directed into the transparent media at the opposite surface 304. Light at a highly oblique angle is rejected by total reflection while the remainder is refracted at this surface and directed towards the edge contour on the opposite surface 304. As the light passes through the transparent media, it impinges on the top-side edge contour 108 surface where it is refracted again and directed towards the objective 210. This light may be dispersed into a range of angles due to surface roughness and defects in the profile.

The objective 210 is an optical element that is used to capture light transmitted through the transparent media 100 and, in some cases, transfer it to a sensor. In further cases, any suitable optical element may be used. Typically, it has its principle axis normal to the transparent media so that it may be used to inspect all edges of the transparent media using simple movements of the transparent media or of the sensing elements. In one embodiment, the objective 210 may collect peripheral light emerging from the transparent media at an angle relative to the plane of the transparent media which approximately facilitates the optical arrangement. In further cases, the angle may also allow for complete illumination of rounded edge profiles of the transparent media 100.

Light that is emitted from the transparent media 100 emerges at a range of angles which are determined by the surface roughness and variation in angle of the surface, including any defects in the surface. The net refraction of the transparent media 100, which in the present example comprises a chamfer, acts like a 45 degree prism in the optical path. The chamfer results in the light being emitted at a substantially different angle than the incident light. Upon exiting the transparent media 100, the light is collected by the objective 210. Since the light emitted is typically not normal to the surface of the transparent media 100, but in some cases it may be desirable for the objective 210 to be normal to the surface of the transparent media 100, the objective 210 is generally positioned off-axis relative to the top-side edge contour 108. This positioning may optimize light collection by keeping substantially all light emitted from the top-side edge contour 108 surface within the acceptance angle of the objective 210. By arranging the angular distribution of incident light 302 and positioning the objective 210 such that its acceptance contains a larger range of related angles of light exiting the transparent media 100, the effect of surface imperfections is reduced or minimized.

The edge decoration 104 may be inspected using the directed light 302. The light collected by the objective 210 may be formed into an image 306 of this decoration 104 as a backlit image. Additionally, as the total light transmitted and collected is mostly affected only by the decoration 104, the opacity of the decoration 104 can be judged.

Figure 4:
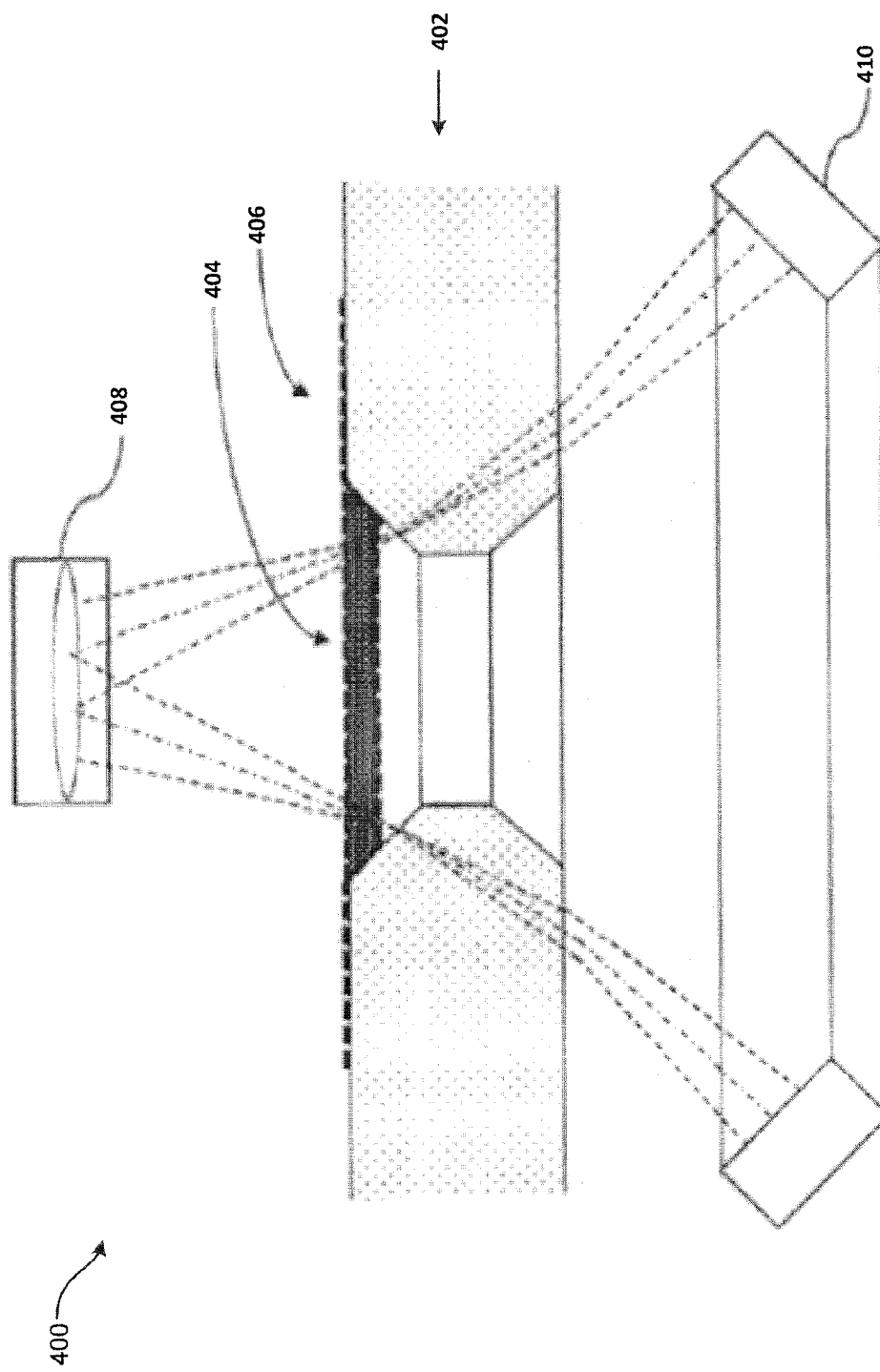
FIG. 4 is a cross-sectional view showing an embodiment of the general optic arrangement as it is applied to a circular aperture in the transparent media.

FIG. 4 illustrates a cross-sectional view of a system for transparent media edge decoration inspection 400, according to another embodiment. The system 400 in this embodiment is applied to a circular aperture 404 in a transparent media 402 with a top-side decoration 406. The system includes an objective 408 and an illuminator 410. The illuminator 410 is a device which provides directed light for inspection purposes.

The objective 408 may be used to inspect a portion of an inside curved edge of a circular aperture 404. In further cases, the objective 408 may be used to inspect the entire opening of the aperture 404 if that opening is of sufficiently small size such that it fits within the aperture of the objective 408, and in some cases, within the field of view of a sensor. In this embodiment, the intrinsic radial geometry of the sensing optics is exploited using the illuminator 410 with a generally circular shape. This could take the form of a physically curved illuminator 410, such as a ring light. In other cases, the illuminator 410 could be a planar illuminator 410 having a curved aperture, or having auxiliary optics, such as a lenticular optic, which could provide the necessary distribution of the directed light. In further embodiments, the aperture 404 can be other suitable shapes; for example, a slot with rounded ends, apertures with rounded corners, or the like.

Additionally, the arrangement can be reversed such that a rounded outside corner of an aperture 404 of a transparent media 402 can be similarly inspected. The transparent media 402 may incorporate various apertures 404, such as holes and slots with interior edges in the transparent media 402 that are at least partially rounded. Inspection of aperture 404 features may be more critical because they are generally not enclosed by other packaging elements such that decoration 406 defects may be more visible.

Figure 5:
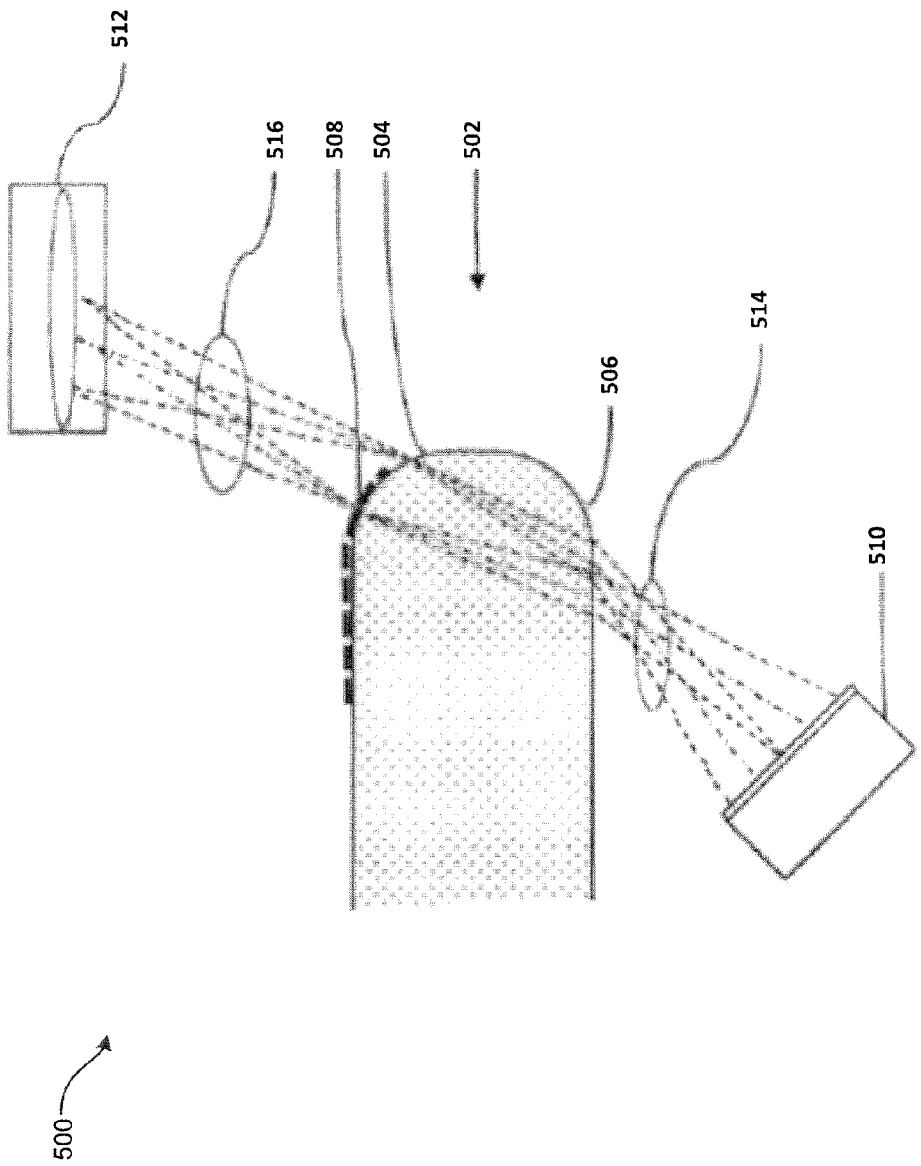
FIG. 5 is a cross-sectional view showing an embodiment of the general optic arrangement as it is applied to a transparent media with a rounded edge profile.

FIG. 5 illustrates a cross-sectional view of a system for transparent media edge decoration inspection 500, according to another embodiment. The system 500 includes an illuminator 510 and an objective 512. The system 500 is applied to a transparent media 502 with a rounded edge profile. The transparent media 502 has a top-side rounded edge 504 and a bottom-side rounded edge 506. The transparent media 502 also includes a decoration 508. The illuminator 510 is a device which provides directed light for inspection purposes.

The embodiment of FIG. 5 differs from a transparent media 502 with a chamfered edge because the directed light 514 from the illuminator 510 may provide a larger range of angles of incidence, such that there is sufficient light emitted from the edge contour which can be captured by the imaging system. In further embodiments, the transparent media 502 may have other edge contour shape profiles, especially as edge finishing may include grinding, polishing, or buffing.

In FIG. 5, the illuminator 510 provides directed light with an angular distribution 514. The illuminator 510 is positioned so that it is not within the field of view of the objective 512, except by bending of the light emitted by the transparent media 502. The objective 512 is an optical element used to capture light transmitted through the transparent media 502 and, in some cases, transfer it to a sensor. In further cases, any suitable optical element may be used. In order to inspect approximately all edges of the transparent media 502 using relatively simple movements of the transparent media 502 or the system 500 elements, the objective's 512 principle axis may be situated normal to the top-side surface of the transparent media 502.

The directed light 514 is directed towards the transparent media 502 at an oblique angle, within a predetermined range of angles. In this embodiment, directed light 514 is directed towards single points on the top-side edge contour 504. In most cases, the directed light 514 is generally emitted as a beam sufficiently wide to at least illuminate the entire edge portion of the transparent media 502. The range of angles of the directed light 514 effectively determines the numerical aperture of the objective 512, and consequently, the depth of focus of the objective 512 such that it may produce an image of the edge contour 504.

In most cases, the distribution of light 514 provided by the illuminator 510 may be varied to coincide with the variance of the general angle of incidence. The angle of incidence may be varied to be in accordance with the surface orientation of each point along the top-side edge contour 504. Although, in the example of FIG. 5, a limited angular distribution is shown at each point, either the illuminator 510 or the aperture of the objective 512, or both, may be used to determine the effective cone of light used to illuminate the edge points.

The bottom-side edge contour 506 of the transparent media 502 is the surface where illumination 510 is directed into the transparent media 502. Light at a highly oblique angle is rejected by total reflection while the remainder is refracted at this surface and directed towards the top-side edge contour 504. Directed light 514 passing through the transparent media 502 impinges on the top-side edge contour 504 where it is refracted again and directed towards the objective 512. This light may be dispersed into a range of angles due to surface roughness and defects in the profile.

The illuminated image 516 results from light emitted from the transparent media 502. The light emerges at a range of angles determined by the surface roughness and variation in angle of the surface, including those resulting from any defects in the surface. The net refraction of the transparent media 502, which in the embodiment of FIG. 5 is a curved contour with an approximation of convex lenses, results in this light being emitted at a substantially different angle than the incident light. The light is collected by the objective 512. Since the emitted light is typically not normal to the surface of the transparent media, but it is desirable that the objective 512 be normal, the objective 512 is generally positioned off-axis relative to the edge. This positioning allows the system to optimize light collection by keeping substantially all light emitted from the contour surface within the acceptance angle of the objective 512. By arranging the angular distribution of incident light of the directed light 514 and the positioning the objective 512 such that its acceptance contains a larger range of related angles of transmitted light of the illuminated image 516, the effect of surface imperfections and curvature is minimized. Since a rounded edge contour 504 approximates a converging lens, light from a substantially curved surface can be captured by a practical objective 512.

The edge decoration 508 may be inspected using the directed light 514 from the illuminator 510. The light collected by the objective 512 may be formed into an image 516 of the decoration 508 as a backlit image. Additionally, the total light transmitted and collected is generally only affected by the edge decoration 508, meaning that the opacity of the decoration can be judged.

Figure 6:
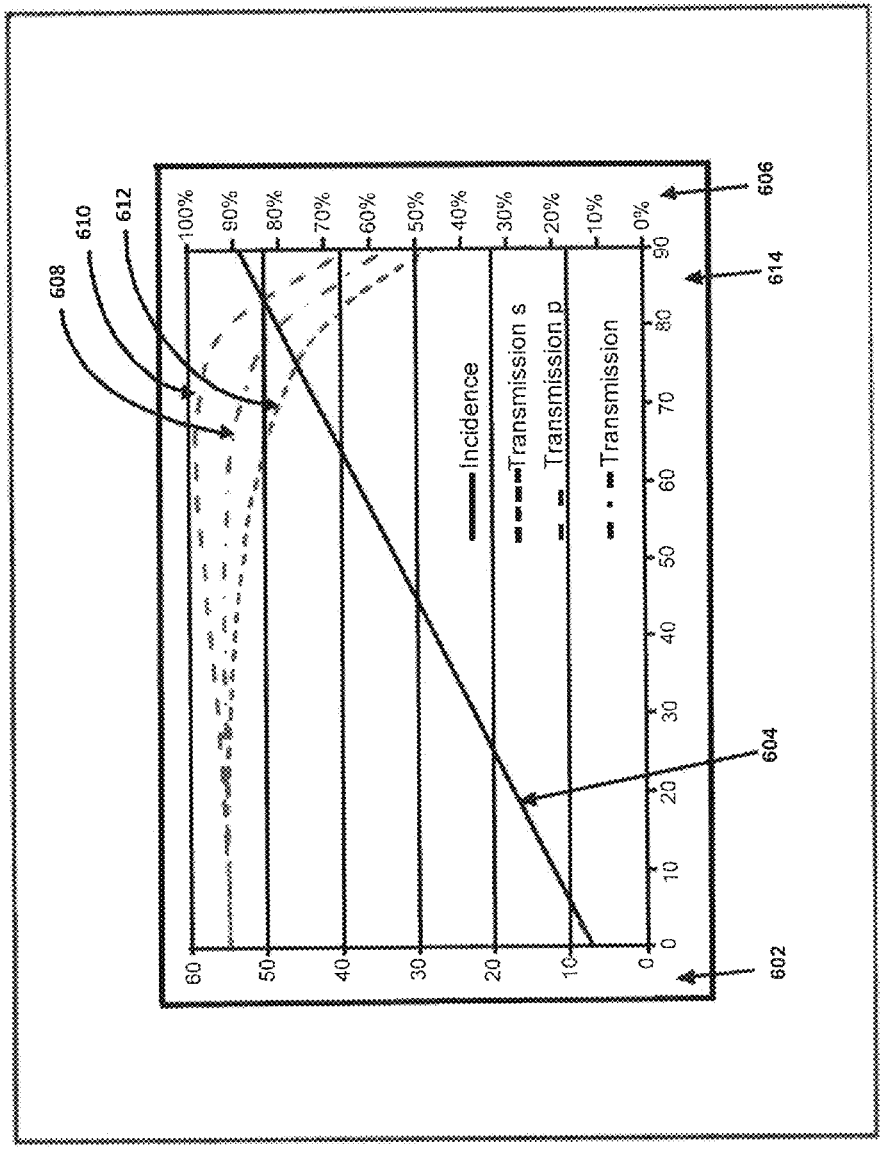
FIG. 6 is a graph showing the properties of an illumination system which produces light transmitted through an edge contour.

FIG. 6 is a graph 600 showing the properties of a system which passes light through a transparent media with an edge contour. The light is provided at the angle which is subtended by the aperture of an objective and the edge contour. In the present case, the angle is approximately 7 degrees relative to the principle axis of the objective; however, other angles may be used. FIG. 6 assumes that the incident illumination has a sufficiently broad angular distribution such that it entirely fills the aperture of the lens with the representative angle being the median value. FIG. 6 illustrates that it is practical to illuminate the majority of the edge contour from below in such a way that the transparent media edge is well lit.

Further, FIG. 6 demonstrates that P-polarized light provides an intended advantage. Uniform intensity or contrast can be obtained by moderate shaping of the angular distribution of the directed light intensity or by adjusting the polarized angle slightly. The difference between P and S polarization is substantial beyond 35 degrees of edge contour slope and substantially linear to about 80 degrees of slope. Thus it is practical to use the difference between P and S polarized images for measuring the edge contour and for identifying chipped out areas of the transparent media.

Contour orientation 614 is represented by the horizontal axis. The contour orientation 614 represents the angle relative to the transparent media surface, with 0 degrees being normal to the plane of the transparent media. Incident angle 602 is represented by the left vertical axis. The incident angle 602 represents the required angle of incidence of directed light on the bottom surface of the transparent media that is needed to provide light exiting from the opposite surface of the transparent media at an angle required for observation using the objective. The incident angle 604 is represented on the graph by the sloped line. The incident angle 604 is the angle required for a desired output angle relative to the orientation of the transparent media surface or edge contour. The required range of incident angles starts at approximately the nominal angle of observing optics and ends at approximately 50 degrees, which is the angle that can be reasonably achieved without entering the direct view of the objective.

The transmission axis 606 is represented by the right vertical axis. The transmission axis 606 represents the proportion of light transmitted through the transparent media having a desired angle on the top-side of the transparent media. Transmission 608 is the proportion of light transmitted through the transparent media at the desired angle, assuming it is unpolarized light. The majority of an edge contour can be illuminated well by incident light at a suitable angle, in the present case, being 85 degrees of slope. The graph distribution also suggests that an essentially uniformly illuminated edge contour can be produced by varying the intensity of the directed light based on angles of incidence.

The proportion of light transmitted for P polarized light 610 is illustrated in the graph. P polarized light can provide greater illumination to an edge contour than otherwise polarized light. P polarized light may be preferred when taking into account that polarization is relative to the edge orientation and the polarizer or analyzer may need to be varied according to edge orientation when multiple edges are inspected.

The proportion of light transmitted for S polarized light 612 is illustrated in the graph. S polarized light may be used to emphasize the edge contour. The ratio of P polarized light to S polarized light arriving at the objective can be used to determine the angle of the surface and therefore, the surface contour from a two dimensional image. This effect of using the ratio can be employed to distinguish coverage defects which can be attributable to the decoration process from those related to a variance in edge contour. S polarized light can also be used to enhance the contrast of the image of the edge of the transparent media.

Figure 7:
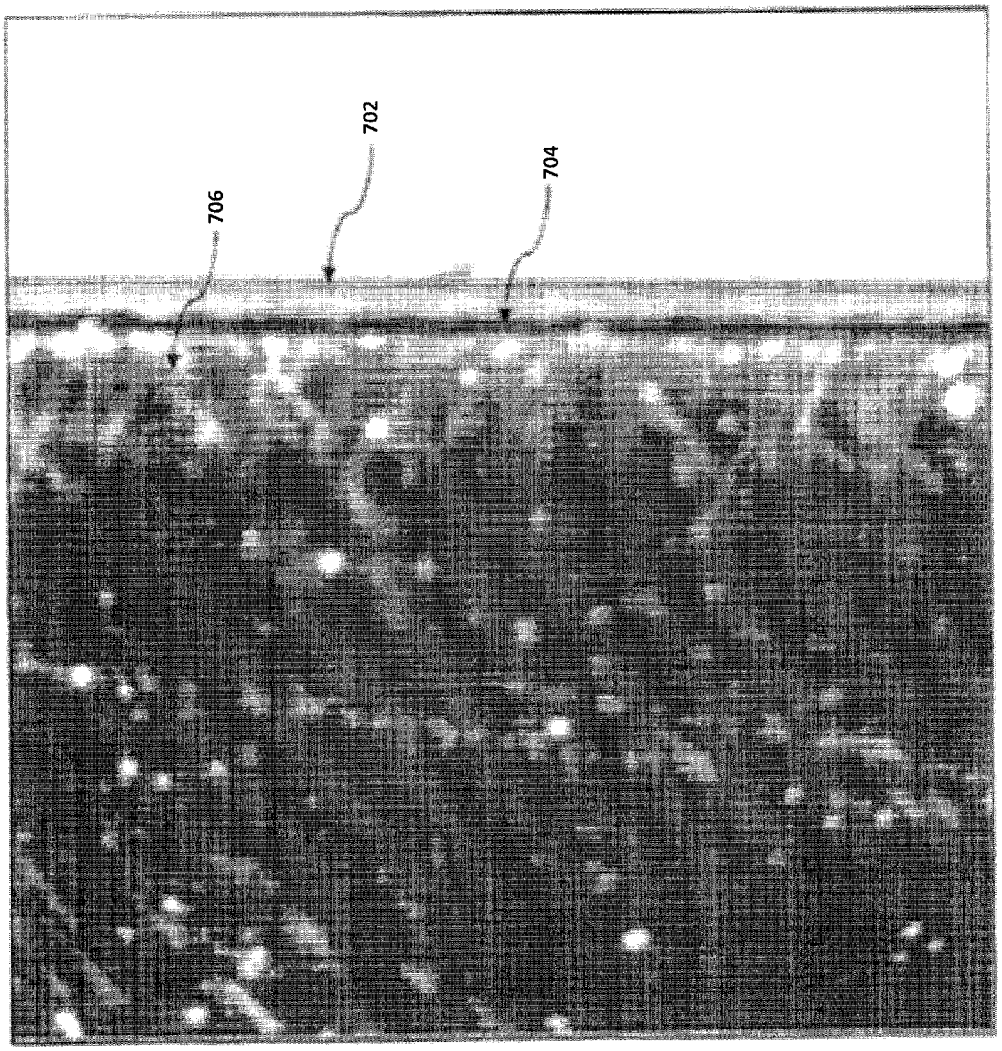
FIG. 7 is an exemplary image obtained from freshly decorated transparent media under normal lighting conditions.

FIG. 7 shows an example image 700 of a section of decorated cover glass near a chamfered edge under conventional illumination. The example image 700 was obtained from freshly decorated cover glass under normal lighting conditions. The image 700 was obtained using normally incident front lighting from a freshly decorated sample.

The glass edge 702 is the edge of the cover glass which is used as a datum for measuring coverage, by a vision system for example, and relative to which coverage of the decoration (for example, ink) is measured. Since this is the datum for the measurement, a crisp, well defined image is preferred in order that image processing algorithms can easily locate the edge and measure its position, preferably to sub-pixel precision. It can be observed that this feature is relatively thin and low contrast. In this image 700, the glass edge 702 is fairly distinct although the intensity slope in the image may limit the ability to measure the edge position to sub-pixel precision.

The decoration edge 704 is the edge of the decoration whose distance from the edge of the cover glass is measured during inspection. The goal is to determine the position of this edge and detect the presence of any defects, for example, smears, bubbles and voids. In this example, location of the edge of the decoration 704 is to a certain extent ambiguous in some places. In the present image, the perimeter of the decoration 704 is moderately distinct but potentially difficult to measure primarily due to the large number of highlights in the interface 706. The decoration edge 704 must meet certain criteria for location and uniformity where it wraps over the edge contour. The goal is to determine the position of this edge and detect the presence of any defects; for example, smears, bubbles, voids, and the like. In this example, location of the edge of the decoration is somewhat ambiguous in some areas; particularly, some projections are associated with seepage of binder material giving a false indication of opacity.

The interface 706 is the pattern of highlights or glare which makes the edge of the decoration more difficult to measure and obscures any voids or thin spots. It can be observed that highlights from texture on the surface of the decoration create considerable interference and obstruction to an analysis of the edge of the decoration. In this example, the residual pattern of the fabric of a silk screen (diagonal linear highlights) can be seen in the wet ink along with bright spots associated with escaping gas bubbles. In some instances, these artifacts may be eventually inconsequential as the wet ink will subsequently level out; however, these artifacts are likely a problem where the system must be able to an in-line post-decoration inspection under these conditions. As can be seen in the image 700, diagonal linear highlights are the residual impressions of a screen used to apply the decoration using a screen print process. A number of bright spots are mainly emerging gas bubbles. The distinct wave may be due to slight variations in ink flow. All of these features provide a measure of the process performance; however, they tend to obscure the location and density of the decoration layer.

Figure 8:
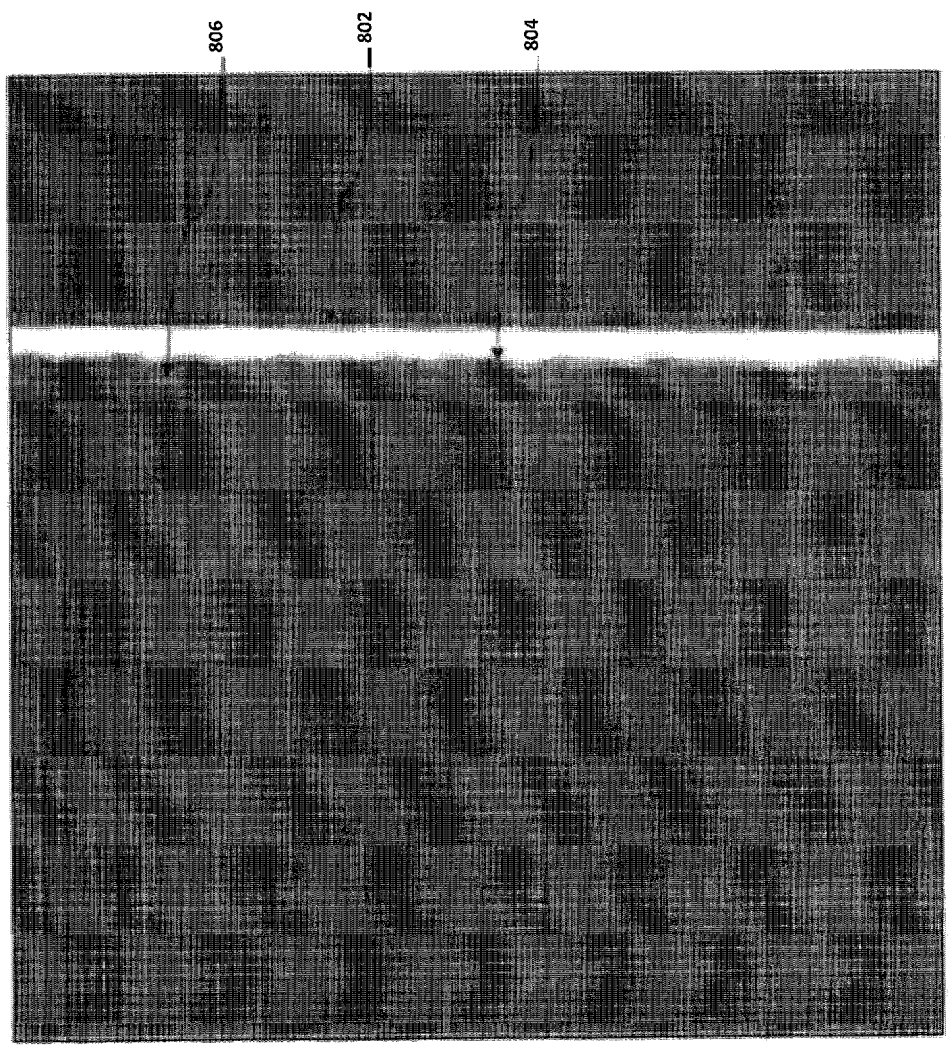
FIG. 8 is an exemplary image obtained from freshly decorated transparent media under illumination according to an embodiment of the present disclosure.

Bright artifacts in the interface 706 make it more difficult to judge coverage of the decoration. It can be observed that highlights from texture on the surface of the decoration create considerable interference and obstruction to an analysis of the edge of the decoration. FIG. 8, according to an embodiment herein and described below, illustrates some true coverage defects that are not apparent in the example of FIG. 7.

FIG. 8 is an exemplary image 800 of a freshly decorated cover glass with a contoured edge under the inspection arrangement of an embodiment described herein. This image is contemporaneous with the image shown in FIG. 7 and demonstrates some of the intended advantages of the described embodiments, especially with regard to the visibility of minor coverage defects.

The glass edge 802 is the edge of the cover glass which is used as a datum by, for example a system for cover glass inspection. Coverage of the decoration (for example, ink) is measured relative to this glass edge 802 datum. The glass edge 802 is seen as a relatively clean and monotonic transition of contrast while the adjacent background is uniformly dark. Since this is the datum for the measurement, a crisp, well defined image 800 is preferred so that image processing algorithms can easily locate the edge and measure its position, preferably to sub-pixel precision. It can be observed that this feature is clearly defined and appears as a single transition in intensity, facilitating detection and measurement of position. It is also an intended advantage that the example image 800 provides greater inspection capabilities than an image obtained with ordinary backlighting.

The decoration edge 804 is the edge of the decoration whose distance from the edge of the cover glass is measured during inspection. The goal is to determine the position of this edge and detect the presence of any defects, for example, smears, bubbles, voids, or the like. In this example image 800, location of the edge of the decoration 806 is clear and readily measured.

Defect 806 is a minor defect in coverage near the edge of the decoration. It can be observed that even minor defects, such as thinning of the ink, are clearly visible and unobstructed, making it possible to better qualify the decoration process. Such minor defects 806 in coverage are visible in the example of FIG. 8 while such defects are near impossible to measure in the previous example of FIG. 7.

Figure 9:
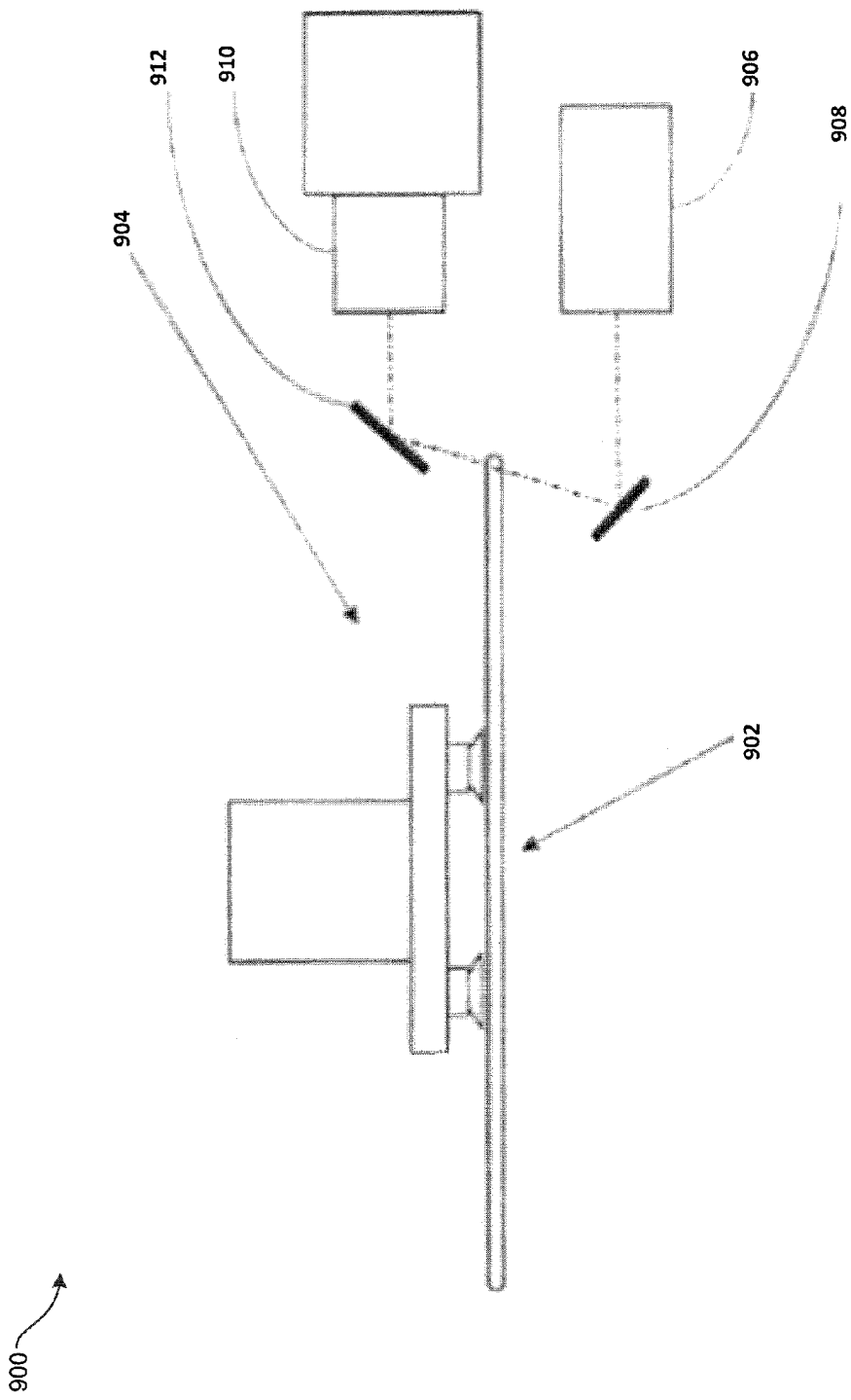
FIG. 9 is a block diagram showing an exemplary inspection setup where the transparent media is held from the top side while the edge decoration is inspected.

FIG. 9 is a block diagram of a system for transparent media inspection 900, according to another embodiment. The system includes a handler 904, an illuminator 906, a first mirror 908, an objective 910 and a second mirror 912. In some cases, the first mirror 908 and/or the second mirror 912 may be adjustable.

FIG. 9 illustrates edge inspection with top/decorated side handling, where decoration (not shown) is present on the same surface used for part handling. It is an example of an inspection setup where the transparent media 902 is held from the top/decorated side while the edge decoration is inspected. As shown, optical paths use first and second foldable mirrors 908, 912 in order to minimize obstruction to part handling. This minimization of the obstruction of the handler 904 allows for various applications. For example, one application may be where parts are handled from above by a robotic manipulator. This embodiment illustrates how, by use of a turning mirror 908, 912, the median optical path can be moved to the center of the objective 910, which potentially minimizes pin cushion distortion. These two aspects may be employed in combination or separately.

Transparent media 902 is presented for inspection of its edge decoration. The transparent media 902 is carried by a handler 904, for example a vacuum gripper or any other gripping device. The handler 904 may be associated with a part handler such as a robot, overhead gantry stage, or the like. It is intended that use of the handler 904 may provide convenient in-line inspection of transparent media 902; for example, during transfer out of a fixture where the transparent media 902 has been decorated. Various exterior edges and apertures may be presented by translating and rotating the transparent media 902 being inspected.

The illuminator 906 is a light source providing directed light as described previously for the purpose of inspecting transparent media. The first mirror 908 depicts a mirror or prism which redirects light from the illuminator 906 towards the item being inspected at the desired angular incidence. While a first mirror 908 is depicted, in other cases the mirror 908 can be curved which would serve a secondary purpose by modifying the distribution of light illuminating the transparent media. The first mirror 908 permits the illuminator 906 to be placed in some other location for various purposes, for example, to increase clearances to facilitate mirror handling. A further benefit is that the angle of the first mirror 908 can be adjusted in order to vary the angle of incidence of the directed light.

The objective 910, or any other sensing device, is a device used to receive light transmitted through the part in order to perform an inspection. The objective 910 may include a camera, a camera connected to an automated image analysis system, a viewing optic for manual observation, or the like. The second mirror 912 depicts a mirror or prism which redirects light from the item being inspected towards the objective 910. The second mirror 912 may be used to improve clearance by enabling the objective 910 to be placed away from the area occupied by the mirror handler 902 and/or the mirror handler's manipulator. In the present example, the objective 910 is to one side. In other cases, the objective 910 could be mounted in other locations, for example, below the plane of the transparent media 902. Additionally, the second mirror 912 can be used to move the median optical path to the center of the objective, eliminating any potential pin-cushion/smile distortion of the image of the edge being inspected, as opposed to the downward viewing previously described where the objective 910 may be placed to one side. In further embodiments, there may be more than two mirrors in any suitable arrangement.

Figure 10:
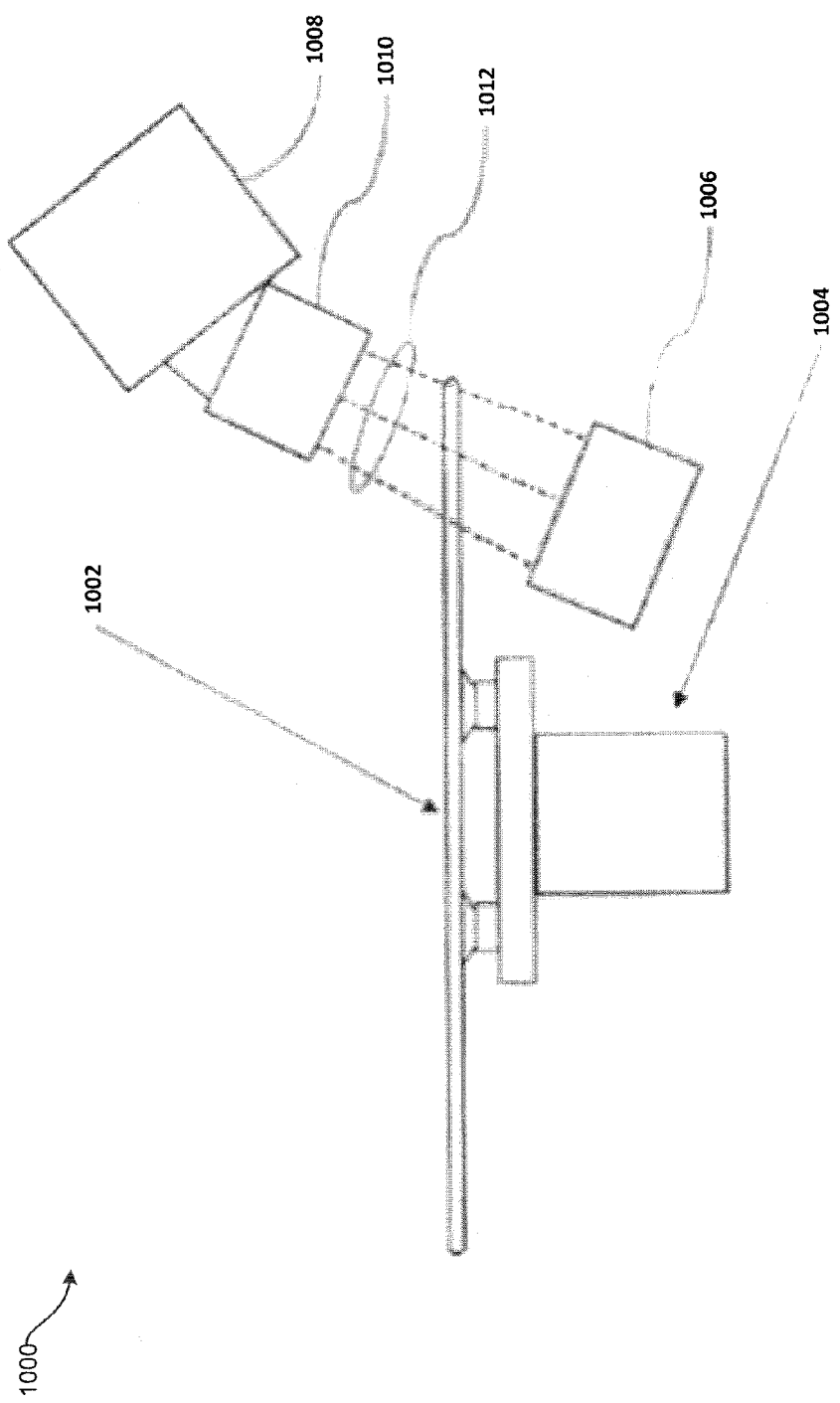
FIG. 10 is a block diagram showing an exemplary inspection setup where the transparent media is held from the bottom side while the edge decoration is inspected.

FIG. 10 illustrates a block diagram of a system for transparent media inspection 1000, according to another embodiment. The system 1000 includes a pedestal 1004, an illuminator 1006, a sensor 1008 and an objective 1010. The illuminator 1006 is a device which provides directed light for inspection purposes.

The system 1000 allows for edge inspection with handling of a transparent media 1002 on the undecorated side. The undecorated side may be the bottom and/or the side opposite the decorated surface. The system 1000 arranges the transparent media 1002 to be held from the undecorated side while the edge decoration is inspected. In this embodiment, optical paths are shown in a configuration consistent with the Schelmplug principle. Consistency with the Schelmplug principle enables the decoration on the edge of the transparent media 1002 to be inspected while simultaneously permitting the decoration that is near, but not on the edge, to be also inspected. The Schelmplug imaging principle may be applied in conjunction with the directed light from the illuminator 1006 in order to expedite part inspection.

The Field of view (FOV) 1012 of the objective 1010, which is a 2-D imaging device, may be used effectively to inspect a larger area of the decoration, including decoration that is at some distance from the edge profile. In some cases, bending the optical path will move the optical path for imaging the edge decoration to the opposite side of the objective 1010. These two aspects may be employed in combination or separately.

Transparent media 1002 is decorated transparent media being presented for inspection of edge decoration as well as the remaining decoration. The pedestal 1004 is a device for holding the transparent media 1002 by the side opposite to the decoration. The pedestal 1004 can be, for example, a vacuum chuck, a simple mechanical support, or the like. The pedestal 1004 presents an alternative means of handling parts during inspection. For example, it can be mounted on a moving element of a conveyor system, which allows the conveyer system to present various portions of the part for inspection. In another case, the pedestal 1004 may be fixed while the inspection assembly components are moveable.

The illuminator 1006, in this instance, may provide directed light for both edge decoration inspection and general inspection of decoration opacity. In other embodiments, the illuminator 1006 may be incorporated into the pedestal 1004. Additionally, the illuminator 1006 could employ a mirror similar to first mirror 908 shown in FIG. 9.

Sensor 1008 is an area sensor that can be used to capture an image of edge decoration from the light gathered by the objective 101. The image may include an image of the surface decoration away from the edge of the transparent media 1002. The configuration of the present embodiment allows for efficient use of the field of view of the objective 101 and the illuminator 1006.

Objective 1010 is configured such that while the edge decoration is viewed at an appropriate viewing angle, the surface of the transparent media 1002 is kept in focus. This arrangement permits rapid inspection of both the edge and the remaining area of decoration with a single inspection assembly. Objective 1010 and sensor 1008 are disposed so that they have an angular arrangement satisfying the Scheimpflug principle.

As shown in the Field of view (FOV) lines 1012 illustrated in FIG. 10, the optical path used in the present embodiment to provide inspection of the transparent media 1002 can encompass a substantial portion of the decoration on the transparent media 1002. This portion can include coverage over a contoured edge of the transparent media 1002.

Figure 11:
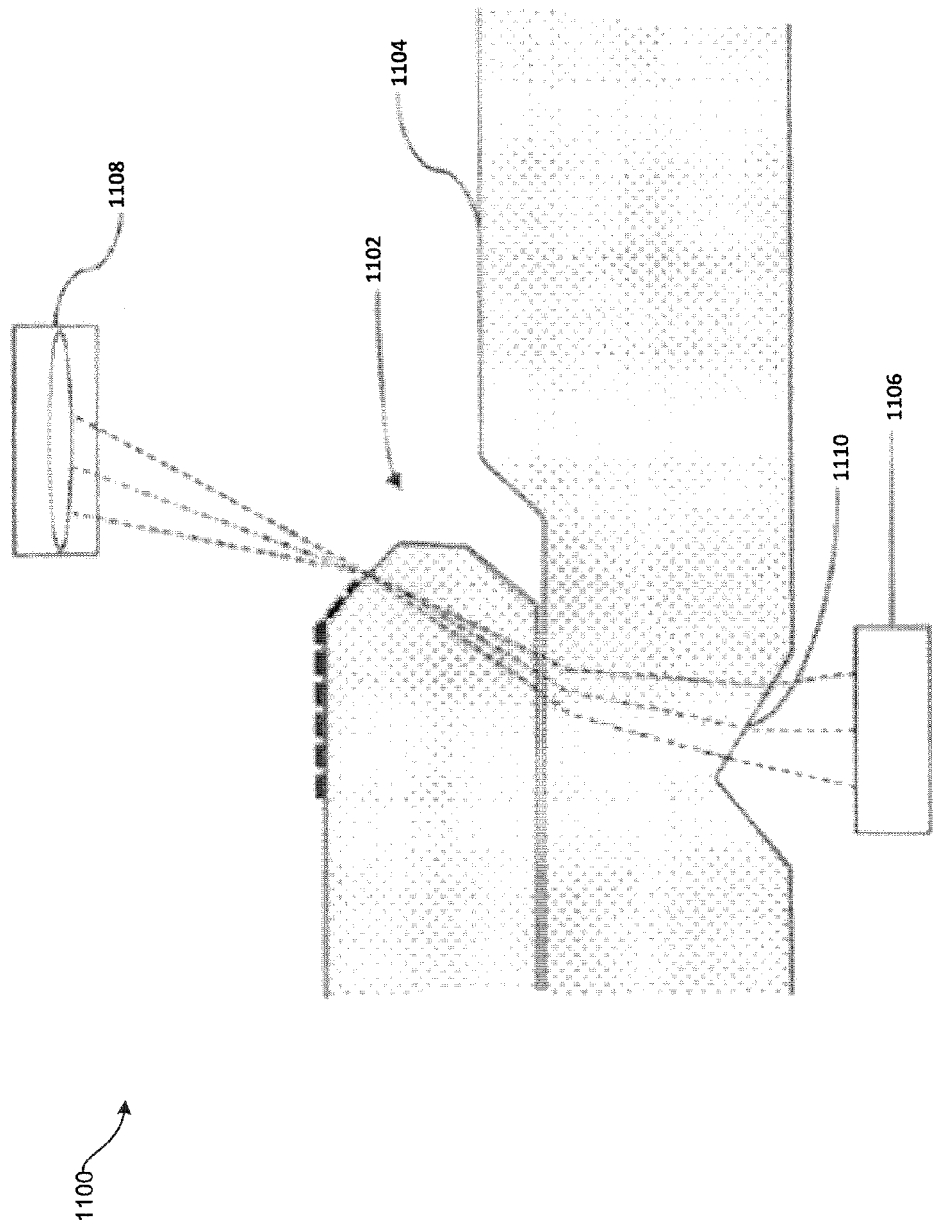
FIG. 11 is a cross-sectional view showing an exemplary inspection setup where the transparent media is held from the bottom side while the edge decoration is inspected with the fixture composed partly or entirely from a transparent material.

FIG. 11 is a cross-sectional view of a system for transparent media inspection 1100, according to another embodiment. The system 1100 includes a fixture 1104, illuminator 1106 and an objective 1108. There may be an optical modifier element 1110 formed into the fixture 1104. The illuminator 1106 is a device which provides directed light for inspection purposes.

The system 1100 is an edge inspection system with a transparent fixture 1104 for transparent media holding. In the example of FIG. 11, the inspection setup arranges a transparent media 1102 to be held from the bottom/undecorated side while edge decoration is inspected. The fixture 1104 is composed partly or entirely from a transparent material which provides broad support, while permitting light access from below the parts as needed for various inspection tasks. The fixture 1104 facilitates inspection of edge decoration, but also provides support such that the same fixture 1104 may be used for other tasks; for example, decoration by screens print, tampo print, or the like. Additionally, this embodiment provides the possibility of modifying the profile of the fixture 1104 in order to provide some additional optical function, as described below.

Transparent media 1102 is presented for inspection of edge decoration as well as other portions of the decoration. The fixture 1104 is a transparent, translucent or partly transparent fixture which supports the transparent media 1102 while providing light access from below the parts. It provides distributed support and may be used to hold one or more transparent media 1102 during inspection, as well as for other processes. The fixture 1104 may be made from durable compounds, such as glass, glass ceramic, or the like, or from less durable but inexpensive compounds, such as polymer or the like. The fixture 1104 may provide full support to one or more transparent media 1102 being processed, while leaving the space below the fixture 1104 uncluttered. Accordingly, it allows for lighting to be configured for inspection of edge decorations in addition to other functions, for example, registration and alignment of parts, inspection of a smear or smudge in the viewing area of the transparent media 1102, or the like. The fixture 1104 can also enable the use of moveable or interchangeable illuminators 1106 without obstruction by part handling mechanisms. In some cases, the fixture 1104 may also be moveable.

The illuminator 1106 is a light source as previously described and is located beneath the fixture 1102. The illuminator 1106 can be further accompanied by optical devises to control, for example, polarity, distribution of intensity, spectrum, or the like.

Objective 1108 is the objective of a sensing device which may be used to inspect the transparent media 1102. The objective 1108 may be moved relative to the fixture, or the fixture may be moved relative to the sensing device, in order to inspect the entirety of one or more transparent media 1102.

The optical modifier element 1110 may be formed into the fixture 1104. In the example of FIG. 11, the optical modifier element 1110 is a prism that can redirect the light from the illuminator 1106, located in the same plane as the fixture 1104, to an appropriate angle for the inspection of edge decoration. In other cases, the optical modifier element 1110 can have a profile that acts as, for example, lenses, diffusers, or the like. In further cases, the optical modifier element 1110 could include various qualities, for example, a series of finer ridges, pits, or the like. Having the optical modifier element 1110 can minimize the cost and complexity of inspection optics. The angle of incidence for each portion of the transparent media 1102 can be customized to the orientation of the feature being inspected without using any moving parts, even where the illuminator 1106 itself is moved to each inspection position as needed.

Figure 12:
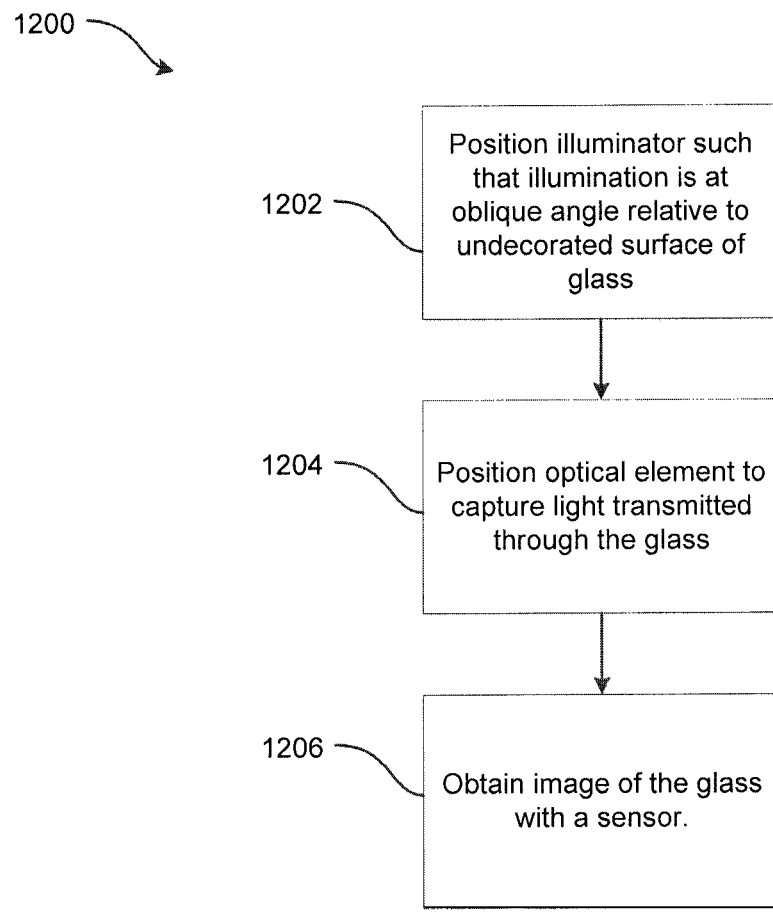
FIG. 12 is a flow-chart for a method of decoration inspection on transparent media, according to an embodiment.

FIG. 12 is a flow-chart for a method of decoration inspection on transparent media 1200, according to an embodiment. At 1202, an illuminator is positioned for directing light at a transparent media. The illuminator directs the light at the transparent media at an oblique angle relative to a surface of the transparent media which is opposite the surface with the decoration. At 1204, an optical element is positioned to capture light transmitted through the transparent media. At 1206, an image of the transparent media is obtained by a sensor from the light captured by the optical element.

In the above embodiments, the location of the transparent media may be determined by tooling such as mechanical datum surfaces, fixturing, or the like. The location of the transparent media may also be determined by guided presentation or placement using a robotic system. Transparent media may also be positioned within the station itself by means of a movable holding fixture which may be guided by the image sensing system or by other sensors.

While positioning the transparent media, other attributes of the transparent media may be obtained, such as determining the edge quality of the transparent media and the outline dimensions of the transparent media. Additionally, auxiliary lighting may be included in order to facilitate other inspections, including lighting for detecting edge defects in the transparent media. This type of inspection may be accomplished in sequence by switching light sources, or concurrently by using wavelength division of light sources. In an example, coverage and opacity may be measured using a red light source, while surface texture, reflectance or some other property of the decoration surface may be measured using a blue light source.

In some cases, the sensor may include switchable spectral lamps and/or one or more spectrally sensitive sensors to measure spectral transmittance of the decoration by measuring opacity at several wavelengths. In one example, the decoration may be visibly opaque but transparent under infrared light. Consequently, visual opacity can be used to distinguish coverage by area and infrared transmittance can be used to distinguish coverage according to thickness of the decoration. In some cases, the same sensor may be used concurrently with conventional backlighting to inspect decoration away from the edge of the transparent media.

The directed light disclosed herein is typically disposed in a linear arrangement to provide the desired illumination of straight edges of the transparent media. However, in other cases, some portion of the illumination may be arranged in an arc to illuminate curved edges. Curved edges may be found, for example, at the corners of transparent media, at the outline of a circular transparent media such as a watch crystal or instrument faceplate, at apertures in the cover plate, or the like. An arced arrangement may also be effective for transparent media with chamfered edges. However, transparent media with radiused edges may require a slight modification of this arrangement. Particularly, the directed light may be arranged to fill a broader range of angles such that the edge contour is essentially uniformly illuminated. In this arrangement, approximately 80% of the edge can be illuminated effectively, which is typically sufficient as decoration usually does not extend more than halfway around the curvature of an edge contour.

The illuminator may have variation in intensity depending on incident angle in order to improve the net uniformity of the result. In a further case, the light may be p-polarized in order to minimize angularly dependent reflections at each surface, which can contribute to uneven illumination over a curved contour. In the case of a radiused edge, the amount of light transmitted through an edge contour is dependent on the polarization of the light where the contour's surface is oblique to the path of the light. This polarization of light may be used to improve the portion of a radiused edge that is well illuminated.

Polarization may be used for any edge profile to estimate slope or curvature of the edge contour by varying the polarization of the directed light between S and P polarization, and then the comparing images. Polarization of the light may be controlled by a polarizer, an analyzer, or both. Polarization is not compulsory but improves upon the number of attributes able to be measured by the system. For example, using polarization to measure the edge contour along with ink coverage, it may be possible to determine whether a coverage defect is the result of a defect in the transparent media edge or a defect in the decoration process, which is significant when used for statistical process control feedback for the decoration process.

In the preceding description, for purposes of explanation, numerous details are set forth in order to provide a thorough understanding of the embodiments. However, it will be apparent to one skilled in the art that specific details may not be required. In other instances, well-known structures are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A system for inspecting a shaped edge area of a transparent media, the transparent media having a decoration on a surface comprising the shaped edge area, the system comprising:
    an illuminator to direct light to the transparent media for inspection, wherein the illuminator directs light to the transparent media at an oblique angle relative to a surface of the transparent media which is opposite the shaped edge area of the surface with the decoration, wherein the illuminator is configurable to vary the intensity of the directed light to uniformly illuminate the shaped edge area of the transparent media;
    a polarizer between the illuminator and the transparent media to modify the polarity of the light from the illuminator to provide p-polarized light or s-polarized light based on the edge orientation of the transparent media;
    a formatter between the illuminator and the transparent media that constrains the angular distribution of the light which illuminates the transparent media;
    an optical element to capture light transmitted through the transparent media; and
    a sensor to obtain an image from the light captured by the optical element.

2. A system according to claim 1, wherein the shaped profile is selected from a group consisting of curved, chamfered, or radiused.

3. A system according to claim 1, further comprising at least one mirror that bends the optical path of the light from the illuminator to allow for adjustment of the transparent media.

4. A system according to claim 1, further comprising a handler to hold the transparent media.

5. A system according to claim 1, further comprising a fixture for supporting the transparent media, wherein the fixture allows light from the illuminator to at least partially pass through the fixture.

6. A system according to claim 5, wherein the fixture includes an optical modifier element formed into the fixture to modify the light from the illuminator.

7. A system according to claim 1, wherein the edge area of the transparent media is an interior edge of the transparent media.

8. A system according to claim 7, wherein the illuminator comprises a generally circular shape.

9. A system according to claim 1, wherein the illuminator further comprises auxiliary optics.

10. A system of claim 1 wherein the formatter is comprised of interchangeable apertures, lenses or holograms.

11. A system according to claim 10, further comprising interchanging the aperture, lenses or holograms of the formatter to modify the distribution of the light which illuminates the transparent media.

12. A method for inspecting a shaped edge area of a transparent media, the transparent media having a decoration on a surface comprising the shaped edge area, the method comprising:
    positioning an illuminator for directing light at the transparent media, wherein the illuminator directs light at the transparent media at an oblique angle relative to a surface of the transparent media which is opposite the shaped edge area of the surface with the decoration, wherein the illuminator is configurable to vary the intensity of the directed light to uniformly illuminate the shaped edge are of the transparent media;
    polarizing the light from the illuminator to provide p-polarized light or s-polarized light based on the edge orientation of the transparent media, via a polarizer placed between the illuminator and the transparent media;
    constraining the angular distribution of the light which illuminates the transparent media, via a formatter;
    positioning an optical element to capture light transmitted through the transparent media; and
    obtaining an image of the transparent media with a sensor from the light captured by the optical element.

13. A method according to claim 12, further comprising configuring the intensity of the directed light from the illuminator to uniformly illuminate the edge area of the transparent media.

14. A method according to claim 12, wherein the illuminator is positioned such that it is not within the field of view of the optical element except by bending of the directed light by the transparent media.

15. A method according to claim 12, wherein the edge area of the transparent media is an interior edge of the transparent media.

16. A method according to claim 12, wherein the optical element is positioned to keep substantially all light emitted from the transparent media within the acceptance angle of the optical element.

17. A method according to claim 12, wherein the illuminator is positioned such that the directed light impinges on the edge of the transparent media and is refracted through the edge area of the surface having decoration towards the optical element.

\* \* \* \* \*